Figure 1:
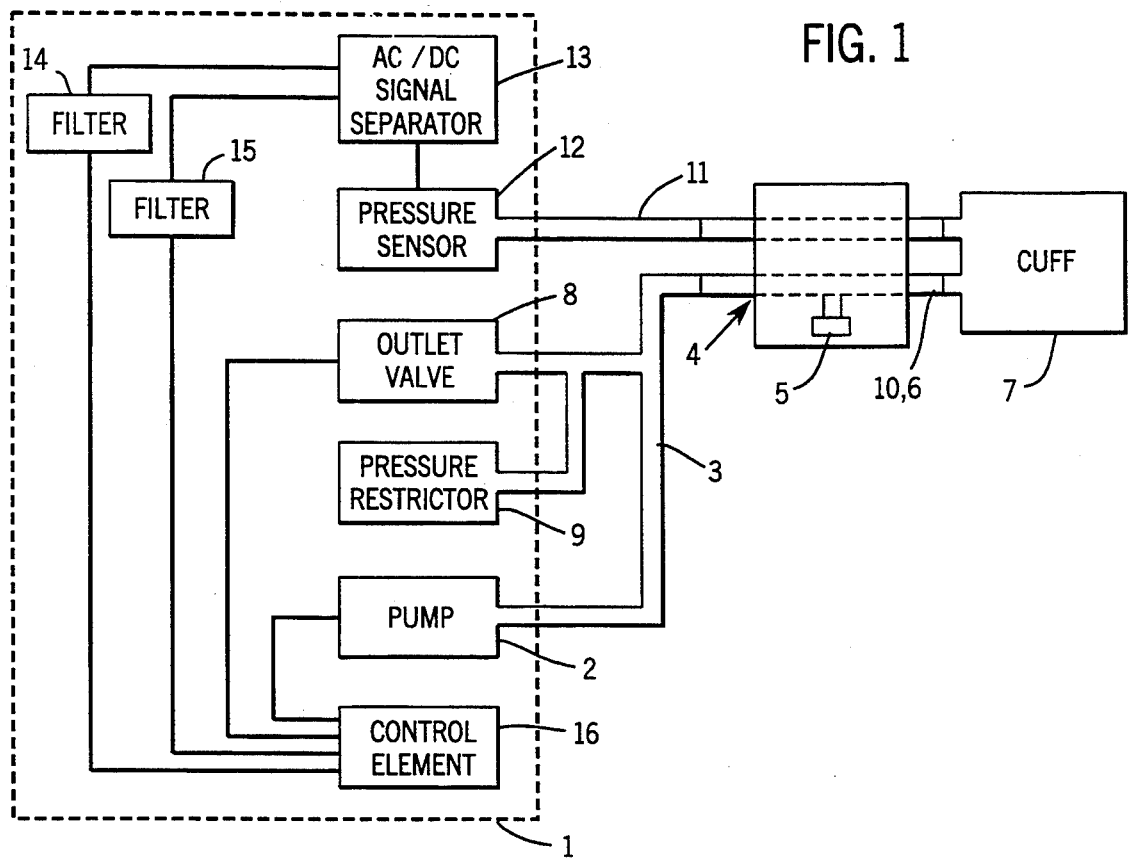

United States Patent [19]

Kankkunen et al.

[11] Patent Number: 5,447,160
[45] Date of Patent: Sep. 5, 1995

[54] RESTRICTION OF PRESSURE IN A CUFF FOR USE IN SPHYGHMOMANOMETRY

[75] Inventors: Lauri Kankkunen, Espoo; Börje Rantala, Helsinki, both of Finland

[73] Assignee: Instrumentarium Corporation, Helsinki, Finland

[21] Appl. No.: 727,088

[22] Filed: Jul. 9, 1991

[30] Foreign Application Priority Data

Jul. 11, 1990 [FI] Finland ................... 903523

[51] Int. Cl.⁶ .............................. A61B 5/00
[52] U.S. Cl. ................... 128/677; 128/681; 128/686; 128/682
[58] Field of Search ........... 128/677, 680–686

[56] References Cited

U.S. PATENT DOCUMENTS

| | | | |
|---|---|---|---|
| 3,527,204 | 9/1970 | Lem et al. | |
| 3,699,945 | 10/1972 | Hanafin | 128/686 |
| 3,929,129 | 12/1975 | Archambault | |
| 4,210,154 | 7/1980 | Klein | |
| 4,953,557 | 9/1990 | Frankenreiter et al. | 128/681 |
| 5,003,981 | 4/1991 | Kankkunen et al. | 128/686 |
| 5,022,403 | 6/1991 | LaViola | 128/685 |
| 5,031,131 | 7/1991 | Kawamura et al. | 128/686 |
| 5,060,654 | 10/1991 | Malkamaki et al. | 128/686 |
| 5,143,077 | 9/1992 | Kobayashi | 128/686 |

FOREIGN PATENT DOCUMENTS

| | | |
|---|---|---|
| 2121804 | 8/1972 | France . |
| 2374012 | 7/1978 | France . |
| 1350183 | 4/1974 | United Kingdom . |

*Primary Examiner*—Lee S. Cohen
*Assistant Examiner*—Robert L. Nasser, Jr.
*Attorney, Agent, or Firm*—Andrus, Sceales, Starke & Sawall

[57] ABSTRACT

An apparatus and a method for restricting to a proper level the pressure increase in cuffs (7) for use in non-invasive automatic sphyghmomanometry and connectable with a common monitor (1). The apparatus comprises a pump (2) and a cuff (7) in communication therewith that can be replaced with another type of cuff. The pressure of the cuff is increased by means of pump (2), a valve (8) for releasing the pressure out of cuff (7), a pressure-sensing element (12) for monitoring the development of a cuff pressure, an AC/DC signal separator (13) for separating an AC component from a DC component in a signal received from the pressure-sensing element, and a control element (16) for further processing the information received from the signal separator and for controlling the operation of valve (8). The different cuff types require separate pressure-restricting elements (5 and/or 9), whose maximum accepted set pressures differ from each other and which automatically drop the cuff pressure as the pressure exceeds a set level.

15 Claims, 1 Drawing Sheet

RESTRICTION OF PRESSURE IN A CUFF FOR USE IN SPHYGHMOMANOMETRY

The present invention relates to an apparatus and a method for restricting to an appropriate level the increase of pressure in at least two types of cuffs for use in sphygmomanometry and connectable with a common monitor, whenever the acceptable maximum pressures of such various cuff types differ from each other.

In non-invasive sphygmomanometry or blood pressure testing, the maximum pressure to be pumped in a cuff must be restricted for reasons of a patient's safety, since excess pressure may seriously hurt a patient. This has been solved by fitting a blood-pressure measuring monitor with a relief valve for allowing the excess pressure to discharge from a cuff whenever the pressure exceeds a certain preset limit pressure. This system works well if the purpose is to use just one and the same cuff type in connection with the same monitor.

The various cuff types include primarily a cuff for adults, a cuff for children, and a cuff for infants. Each cuff type carries its own limit values for excess pressure. Thus, it has been difficult to use the same apparatus for various groups of patients since the relief valve has only been able to carry a single limit pressure which can only be applied to a single group of patients. An adjustable relief valve, which would always be re-adjusted with the change of a group of patients, is quite complicated in practice and even hazardous as its re-adjustment can easily be overlooked.

A relief valve is often adjusted according to a group of patients using a cuff that can be pumped to a highest possible pressure. When an automatic measuring apparatus is fitted e.g. with a children's cuff, the limit value for excess pressure can be controlled in a programmable fashion. Thus, the operator must remember to notify the apparatus of the change of a cuff type, otherwise a neglect may cause even serious damage e.g. to a newborn baby. Available are also equipment which identifies a cuff type automatically. However, even such automatic methods are not always sufficiently reliable in operation, since even the programs can be unreliable. Currently, this aspect affecting the patients' safety has begun to draw serious attention.

An object of this invention is to eliminate the above problems. Thus, the object is to provide a reliable and economic method and apparatus for use in sphyghmomanometry, capable of safely measuring blood pressure by using various cuff types, such as e.g. the adults' cuffs, children's cuffs, and infants' cuffs, without allowing the cuff pressure to exceed the limit values for excess pressure set for each cuff type. Another object is to provide a method and apparatus for use in sphyghmomanometry, wherein the excess-pressure limit value for various cuff types is independent of how the apparatus is programmed.

The characterizing features for a system of the invention are set forth in the annexed claims.

In a non-invasive blood pressure measuring apparatus applicable to various cuff types, the proper restriction of a maximum acceptable pressure in a cuff for a group of patients using each cuff type is based on that, during the course of changing a cuff type, the cuff type in question is at the same time connected to such a relief valve, whose acceptable maximum pressure is suitable for this particular cuff type. Normally, the highest acceptable pressure reading for the adults' cuff type is appr. 300 mmHg. For children, the corresponding reading is appr. 200 mmHg and for infants appr. 150 mmHg.

According to the invention, a space in flow communication with a cuff and preferably in association with a tube running from a cuff to a monitor is fitted with a pressure-restricting element which tolerates a pressure acceptable for this particular cuff type to a certain limit prior to the discharge of excess pressure out of the cuff. Thus, a cuff and preferably a pressure-restricting element are replaced simultaneously when replacing a cuff type with another.

Figure 2:
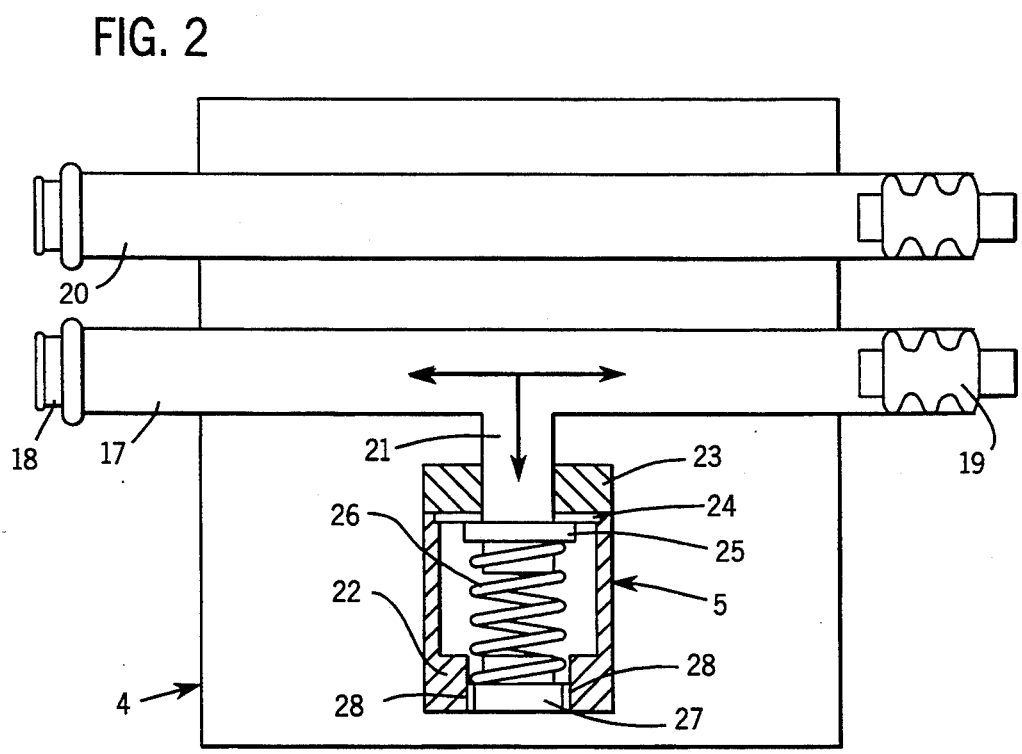

The invention will now be described in more detail with reference made to the accompanying patent drawings, in which FIG. 1 shows a schematic view of an apparatus of the invention applicable to the restriction of a maximum pressure in various cuff types, FIG. 2 shows a split-up view of one preferred intermediate element, intended for use in the embodiment of FIG. 1, connectable with a tube extending to the cuff, and fitted with a conventional pressure-restricting element therein.

Referring to the schematic view shown in FIG. 1, a monitor 1 is indicated by a dash-and-dot line, containing a pump 2 provided with a tube 3 extending to an intermediate element 4 which includes a pressure-restricting means 5. The intermediate element is in communication with a cuff 7 by way of a tube 6. The tube extending between the pump and the intermediate element is also in communication with an outlet valve 8 for discharging air pumped in the cuff, and with another pressure-restricting means 9, preferably included in the monitor. On the other hand, the cuff extends a tube 10 to intermediate element 4 and further a tube 11 extends to a pressure-sensing element 12. A signal received from the pressure-sensing element travels through an AC/DC signal separator 13 and filters 14 and 15 to a control element 16, the latter also controlling the operation of pump 2 and valve 8. The control element is preferably a microprocessor.

The intermediate element 4 is shown as a longitudinally split-up view in more detail in FIG. 2. A benefit offered by a separate intermediate element as compared to a solution, wherein such an element would not be included and a pressure-restricting element would be included in tubes extending between cuff and monitor, is that a tube, which may be quite long in some cases, extending from the monitor need not be replaced when a cuff type is replaced but just an intermediate element suitable for each cuff type along with its pressure-restricting means is replaced as a cuff type is changed.

Thus, a tube 17 included in the intermediate element is connected to a conventional tube 3 by means of fasteners 18 or 19, the latter tube extending from pump 2 to cuff 7. One of the ends of tube 17 included in intermediate element 4 is fitted with a cuff by using a fastener 19 or 18 and through the intermediary of a tube 6. The intermediate element 4 includes also a tube 20 fitted between tubes 10 and 11 extending from cuff 7 to pressure-sensing element 12.

The intermediate element tube 17 is fitted with a pressure-restricting means 5, which is often referred to as a relief valve and used to restrict the increase of pressure of a gas or a fluid not to exceed some certain limit. Tube 17 and pressure-restricting means 5 are in communication with each other by way of an aperture 21. A conventional pressure-restricting means shown in FIG. 2 comprises a body section 22 and a counter member 23. Between the body and the mounter member is fitted a gasket 24 extending across body 2 to insulate a plunger 25 from counter member 23. In the body section, said plunger 25 is pressed against gasket 24 by the action of a spring 26. The other end of the spring is secured to an adjustment element 27. There is a communication from inside the pressure-restricting means to ambient air through an aperture 28.

The operation of a conventional pressure-restricting element is based on the fact that, as the pressure of a gas or a fluid coming in through inlet 21 increases, said pressure tends to urge plunger 25 and its associated spring 26 backwards. When the pressure of a gas or a fluid overcomes the opposing force of spring 26, the plunger will move backwards and, thus, the excess pressure prevailing in tube 17 discharges through a gap formed between gasket 24 and plunger 25 into the interior of the pressure-restricting element and further out of aperture 28. As pressure is dropping in tube 17 and in a space in flow communication therewith, said plunger 25 is pressed by the action of spring 26 against gasket 24 to prevent pressure from discharging this way. The adjustment element 27, preferably a set screw, can be used to adjust or control a force applied to plunger 25 through the action of spring 26.

In the embodiment shown in FIG. 1, a monitor 1 itself is also provided with a pressure-restricting element 9. The maximum pressure accepted by this element, prior to the moment it allows pressure to discharge from a cuff 7, is preferably adjusted in accordance with the requirements of the largest or adults' cuff type. Thus, this pressure-restricting element 9 causes no problems either when the monitor is coupled with cuff types intended for children and newborn babies. However, the coupling of smaller cuffs requires a further pressure-restricting element 5, whose pressure tolerance is set on a level suitable for this very cuff type to be coupled. Both of these smaller cuff types require their own pressures restricting element. As the pressure exceeds this level, an element 5 responding to a lesser pressure is of course triggered instead of an element 9 included in the monitor.

In practice, the replacement of a cuff type is accompanied by fitting tubes 3 and 11 with an intermediate element 4 which includes such a pressure-restricting element 5, whose maximum acceptable pressure is set for exactly that cuff type which is to be coupled therewith. If a cuff type is replaced again, said intermediate element 4 is replaced at the same time with another intermediate element provided with a pressure-restricting element, whose maximum acceptable pressure is compatible with a cuff type to be coupled therewith. When a cuff type is replaced with the largest or adults' cuff type, said tubes 3 and 11 leading to the cuff need not be necessarily fitted with a separate intermediate element 4 along with its pressure-restricting element 5, but the adults' cuff can be directly connected to tubes 3 and 11.

In order not to accidentally couple a wrong type of cuff with an intermediate element 4, provided with a pressure-restricting element 5 releasing at a certain pressure, said intermediate element is preferably fitted with a coupling which is only compatible with a cuff type intended to be connected therewith. It would also be beneficial if smaller cuffs could not be directly coupled with tubes 3 and 11 without an intermediate element 4 including a pressure-restricting element (5).

The invention is by no means limited to the above embodiments but modifications can be made to various details of the invention within the scope of the claims.

The invention is not limited to the location of a pressure-restricting element or to including it in a separate and per se preferred intermediate element but, instead, such pressure-restricting element can be included e.g. in a cuff itself which eliminates the need for any replacements of tubes or intermediate elements or it can be included in a tube generally connected with a cuff. In the embodiment described in reference with the drawings, the monitor included a pressure-restricting element 9. It is obvious that this element 9 is not necessary if the largest cuff type is provided with a separate pressure-restricting element 5, which can be included e.g. in intermediate element 4. In this case, said monitor 1 preferably comprises a pump 2, a valve 8, a pressure-sensing element 12, an AC/DC signal separator 13, and a control element 16. In view of the invention, the most essential feature is that a pressure-restricting element is in flow communication with a cuff and that for each cuff type there is a pressure-restricting element releasing at a suitable pressured thereby the excess pressure of a cuff is allowed to discharge.

We claim:

1. A method for restricting to a proper level the pressure increase in first and second cuffs used in sphygmomanometry, said first and second cuffs to be coupled to a monitor and having first and second maximum acceptable pressures respectively, comprising:
    placing said first cuff in flow communication with said monitor and placing a first pressure-restricting element in flow communication with said monitor;
    inflating said first cuff, said first pressure-restricting element releasing pressure in said first cuff when the pressure in the first cuff is equal to or exceeds said first maximum acceptable pressure;
    measuring the blood pressure of a patient using said first cuff;
    decoupling said first cuff from flow communication with said monitor;
    decoupling said first pressure-restricting element from said monitor after said first cuff has been decoupled and before placing said second cuff in flow communication with said monitor;
    placing said second cuff in flow communication with said monitor and placing a second pressure-restricting element in flow communication with said monitor;
    inflating said second cuff, said second pressure-restricting element releasing pressure in said second cuff when the pressure in the second cuff is equate to or exceeds said second maximum acceptable pressure;
    measuring the blood pressure of a patient using said second cuff;
    decoupling said second cuff from flow communication with said monitor; and
    decoupling said second pressure-restricting element from said monitor after said second cuff has been decoupled from flow communication with said monitor.

2. The method of claim 1, further comprising:
    forming said first cuff integral with said first pressure-restricting element before said first cuff is placed in flow communication with said monitor.

3. The method of claim 1, further comprising:

prefitting said monitor with a third pressure-restricting element corresponding to a third maximum acceptable pressure of a third cuff, said third maximum acceptable pressure being greater than both said first and said second maximum acceptable pressures.

4. The method of claim 1, further comprising:

placing a third cuff in flow communication with said monitor after decoupling said second pressure-restricting element; and placing a third pressure-restricting element in flow communication with said monitor, said third pressure-restricting element releasing pressure in said third cuff when the pressure in the third cuff is equal to or exceeds a third maximum acceptable pressure.

5. The method of claim 1, wherein said first cuff is suitable for use with adult patients, and said second cuff is suitable for use with children.

6. An apparatus for use in sphygmomanometry, comprising:

a pump and a first cuff in communication therewith and replaceable with a second cuff, the pressure in said first cuff being increased by means of said pump;

a valve means for releasing pressure out of said first cuff;

a pressure-sensing means for monitoring the development of a cuff pressure in said first cuff;

an AC/DC signal separator means for separating an AC component form a DC component in a signal received from the pressure-sensing means; and a control means for further processing the information received from the signal separator means and for controlling the operation of said valve means;

wherein said first cuff has a first pressure-restricting element associated therewith, and wherein said second cuff has a second pressure-restricting element associated therewith, said first and second pressure-restricting elements having respective first and second maximum acceptable set pressures that differed from each other and that automatically drop the respective cuff pressure as the pressure in the respective cuffs exceeds a set level.

7. An apparatus as set forth in claim 6, wherein said first pressure-restricting element accepts the maximum possible set pressure and is coupled whenever the largest available first cuff is coupled with the apparatus, and wherein said first pressure-restricting element is integral with the apparatus.

8. An apparatus as set forth in claim 7, wherein said second pressure-restricting element, whose maximum accepted set pressure is lower than a pressure accepted by said first cuff connectable with the same apparatus, is coupled with the apparatus during the replacement of said first cuff by said second cuff.

9. An apparatus as set forth in claim 8, wherein said second pressure-restricting element is located in a place which is in flow communication with said second cuff.

10. An apparatus as set forth in claim 6, wherein said first pressure-restricting element is located in a tube extending from said pump or from said valve means to said first cuff, or is located within said first cuff itself.

11. An apparatus as set forth in claim 6, wherein said first pressure-restricting element is located in a tube extending from the first cuff to the first pressure-sensing means.

12. An apparatus as set forth in claim 6, wherein said second pressure-restricting element is located in a separate intermediate element which is fitted between said second cuff and said monitor during the replacement of said first cuff by said second cuff.

13. An apparatus as set forth in claim 6, further comprising a third cuff, each of said first, second and third cuffs being separately coupled with the apparatus.

14. An apparatus as set forth in claim 13, wherein said three cuffs include a cuff for adults, a cuff for children, and cuff for infants.

15. A method for restricting to a proper level the pressure increase in first and second cuffs used in sphygmomanometry, said first and second cuffs to be coupled to a monitor and having first and second maximum acceptable pressures respectively, comprising:

placing said first cuff in flow communication with said monitor and placing a first pressure-restricting element in flow communication with said monitor;

inflating said first cuff, said first pressure-restricting element releasing pressure in said first cuff when the pressure in the first cuff is equal to or exceeds said first maximum acceptable pressure;

measuring the blood pressure of a patient using said first cuff;

decoupling said first cuff from flow communication with said monitor;

placing said second cuff in flow communication with said monitor and placing a second pressure-restricting element in flow communication with said monitor;

inflating said second cuff, said second pressure-restricting element releasing pressure in said second cuff when the pressure in the second cuff is equal to or exceeds said second maximum acceptable pressure;

measuring the blood pressure of a patient using said second cuff;

decoupling said second cuff from flow communication with said monitor; and said method including the initial step of prefitting said monitor with a third pressure-restricting element corresponding to a third maximum acceptable pressure of a third cuff, said third maximum acceptable pressure being greater than both said first and said second maximum acceptable pressures.

* * * * *